(12) United States Patent
Ko-Wen (10) Patent No.: US 6,241,705 B1
(45) Date of Patent: Jun. 5, 2001

(54) NASAL IRRIGATOR

(75) Inventor: Huang Ko-Wen, Taipei Hsien (TW)

(73) Assignee: Shih-Kang Medical Instruments Co., Ltd., Taipei (TW)

( * ) Notice: Subject to any disclaimer, the term of this patent is extended or adjusted under 35 U.S.C. 154(b) by 0 days.

(21) Appl. No.: 09/440,855

(22) Filed: Nov. 16, 1999

(51) Int. Cl.$^7$ ........................................... A61M 1/06
(52) U.S. Cl. ..................................... 604/73; 604/93
(58) Field of Search ....................... 604/73, 93, 94, 604/514; 128/911, 200.17, 200.18, 200.14, 207.18, DIG. 12; 222/320, 321.1, 32.2, 321.6, 321.7, 321.8, 321.9, 322, 323

(56) References Cited

U.S. PATENT DOCUMENTS 2,135,052 * 11/1938 Rose ........................................ 604/73

FOREIGN PATENT DOCUMENTS

0410318 * 1/1991 (EP) ........................................ 604/73

* cited by examiner

*Primary Examiner*—Manuel Mendez
(74) *Attorney, Agent, or Firm*—Rabin & Champagne, P.C.

(57) ABSTRACT

A nasal irrigator mainly includes a saline container having an upward inclined bottom conduit, a lower cap connected to a free end of the conduit, and a plug fitted around a front tube portion of the lower cap for extending into a patient's nostril. The tube portion of the lower cap is provided around an outer periphery of a front end with an annular rib. A stopper is fixed in and projected forward from the front end of the tube portion such that a passage is formed between the stopper and the tube portion. The plug has a front head portion provided with an axial through hole and a rear sleeve portion adapted to fitly put around the tube portion of the lower cap. The plug may be pushed toward the lower cap so that the stopper extends into and blocks the through hole of the plug, and saline in the container could not be supplied into the plug via the through hole. And, the plug may be pulled forward relative to the lower cap until an annular groove in the sleeve portion engages with the annular rib around the front end of the tube portion, so that saline in the container could be supplied to the plug via the conduit, the passage between the stopper and the tube portion of the lower cap, and the through hole in the head portion of the plug.

6 Claims, 7 Drawing Sheets

(PRIOR ART)
Fig. 1

(PRIOR ART)

Fig. 2

(PRIOR ART)

NASAL IRRIGATOR

BACKGROUND OF THE INVENTION

The present invention relates to a nasal irrigator, and more particularly to a nasal irrigator that can be easily operated to switch between a closed and an open state to disable and enable, respectively, a supply of saline from the nasal irrigator to wash a patient's nostril.

A nasal irrigator referred to herein generally includes a container for containing an amount of saline and a plug for extending into a patient's nostril. By squeezing the container, saline in the container could be supplied into the patient's nostril via the plug in order to wash the nostril.

Figure 1:
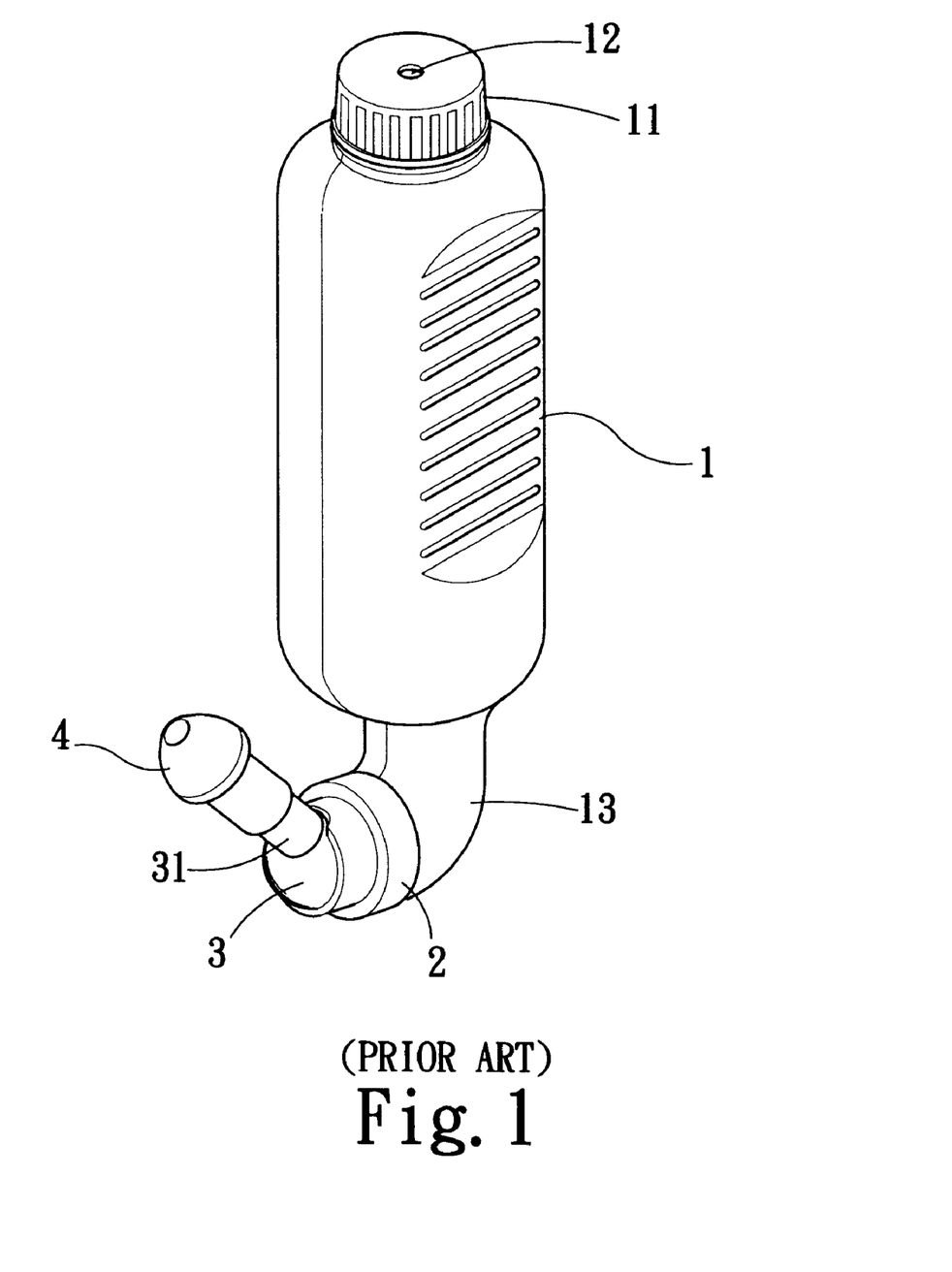
FIG. 1 is a perspective of a conventional nasal irrigator.
Figure 2:
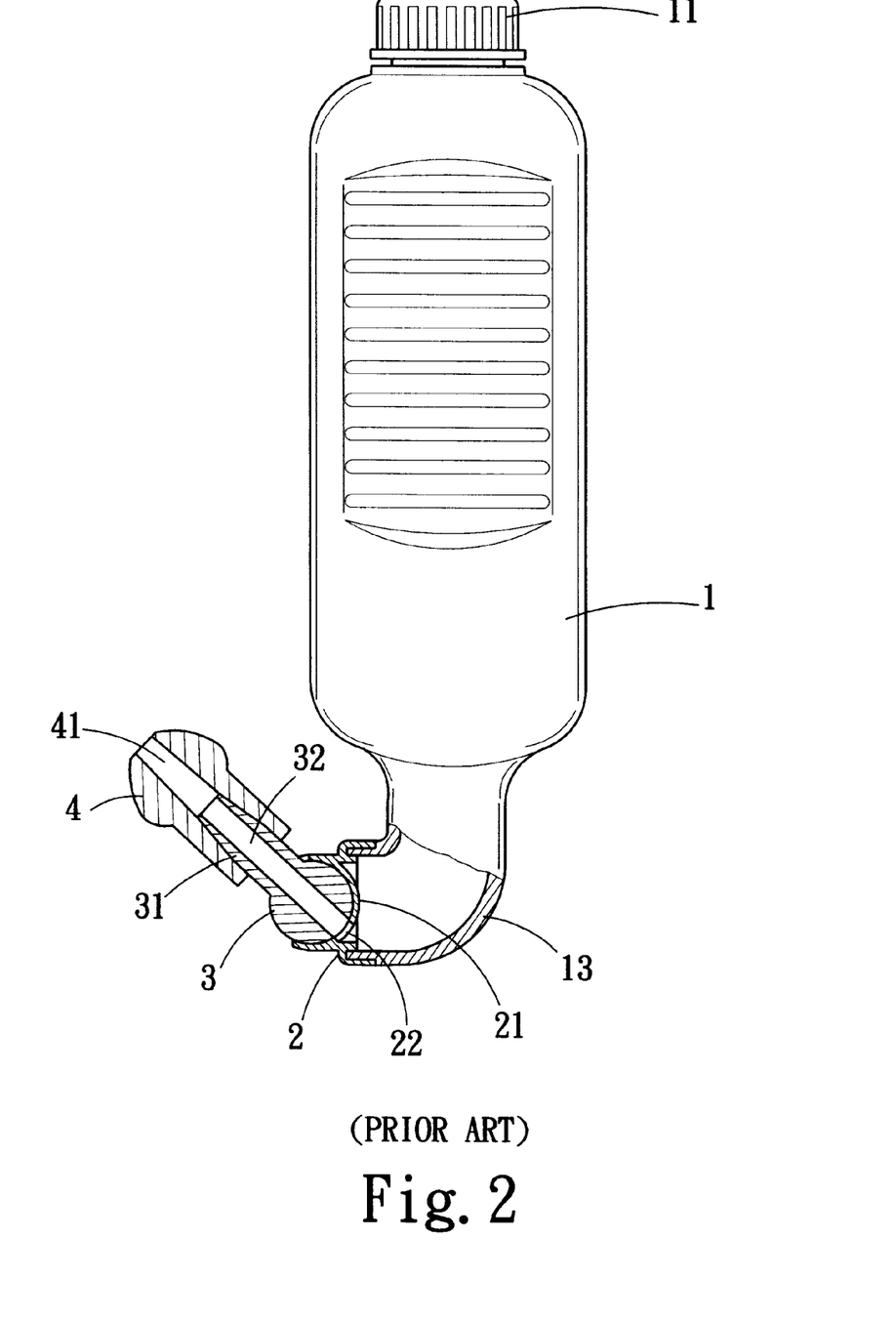
FIG. 2 is a partially vertical sectional view of the conventional nasal irrigator of FIG. 1 in an open state in which saline is supplied from the nasal irrigator into a patient's nostril.

FIGS. 1 and 2 are perspective and partially vertical sectional views, respectively, of a conventional nasal irrigator. As shown, the conventional nasal irrigator mainly includes a container 1 for containing an amount of saline. The container 1 is provided at a top with an upper cap 11 having an air vent 12, and at a bottom with a conduit 13 extended downward and then inclined upward by a suitable distance. A lower cap 2 is connected to a free end of the conduit 13 and has a curved surface to define a substantially spherical recess 21 into which a spherical valve 3 is movably fitted. An opening 22 is formed on the curved surface of the lower cap 2 at a lower portion thereof to communicate the conduit 13 with the spherical recess 21. The spherical valve 3 includes a forward extended tube 31 and a central passage 32 axially extending through the tube 31 and passing through a center of the spherical valve 3 to end at a rear end of the spherical valve 3 facing the spherical recess 21. A plug 4 is put around a front part of the tube 31 and has a shape suitable for inserting into a patient's nostril. The plug 4 has a tapered hole 41 axially extended at a central portion of the plug 4 for receiving the tube 31 therein and communicating with the central passage 32 of the spherical valve 3.

To use the conventional nasal irrigator of FIG. 1, the plug 4 and accordingly the tube 31 received therein are pulled upward relative to the conduit 13, as shown in FIG. 2, so that the spherical valve 3 turns in the spherical recess 21 to allow the tapered hole 41 and the central passage 32 to align with the opening 22 on the curved surface of the lower cap 2. At this point, saline contained in the container 1 is allowed to flow from the container 1 to sequentially pass through the conduit 13, the opening 22, the central passage 32, and the tapered hole 41 into the patient's nostril to wash the same.

Figure 3:
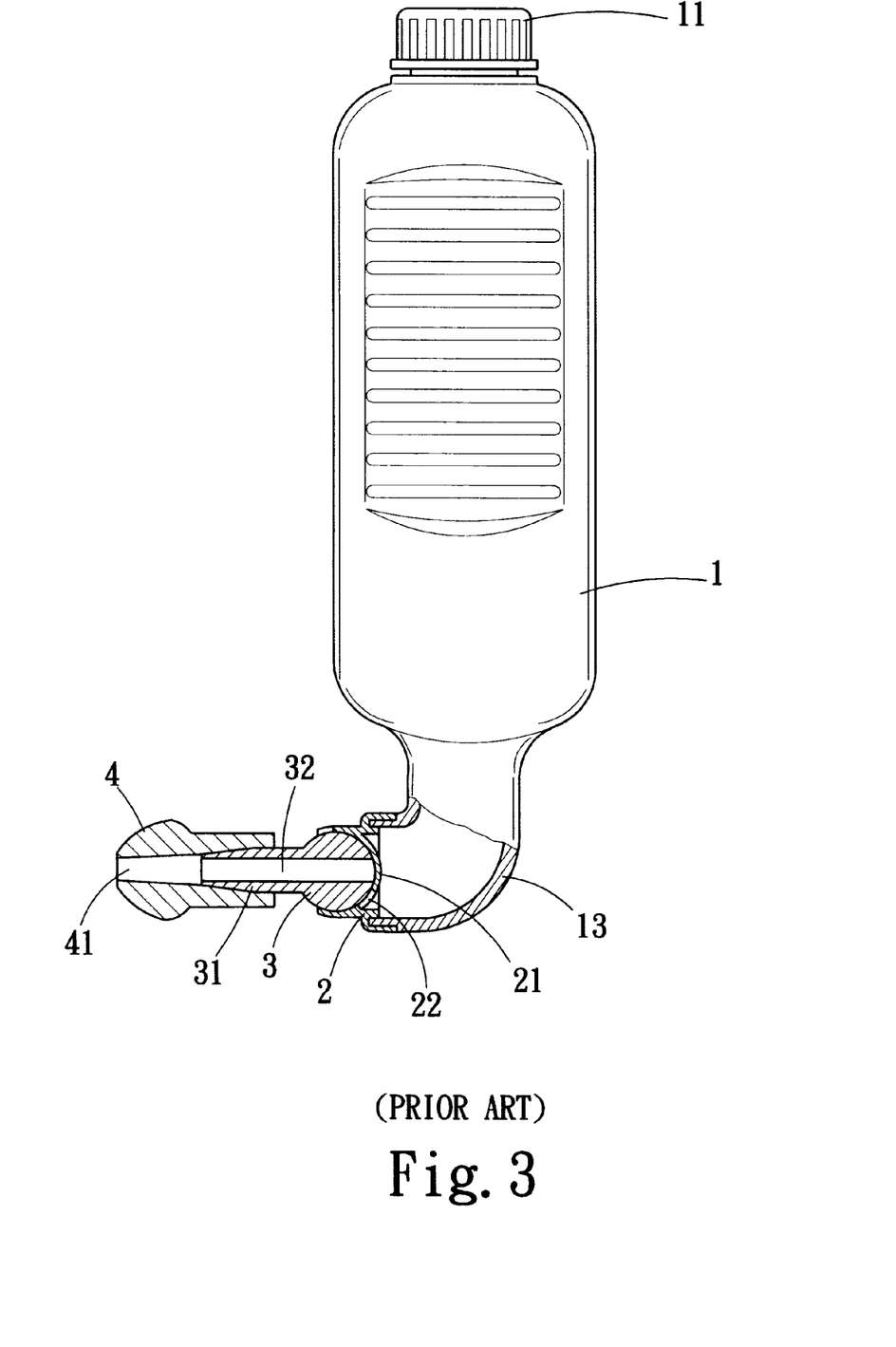
FIG. 3 is a partially vertical sectional view of the conventional nasal irrigator of FIG. 1 in a closed state in which saline could not be supplied from the nasal irrigator to the patient's nostril.

And, when the conventional nasal irrigator of FIG. 1 is not in use, the plug 4 and accordingly the tube 31 received therein are pushed downward relative to the conduit 13, as shown in FIG. 3, so that the spherical valve 3 turns in the spherical recess 21 and the tapered hole 41 and the central passage 32 no longer align with the opening 22. At this point, the opening 22 is closed and the saline in the container 1 could not flow from the conduit 13 to the plug 4 and into the patient's nostril via the opening 22, the central passage 32 and the tapered hole 41.

The following are some of the disadvantages of the above-described conventional nasal irrigator:

1. The spherical valve 3 and the spherical recess 21 of the lower cap 2 must be associated with each other in a tight fit relation to avoid leakage of saline from any clearance between them. These two parts must therefore be manufactured with very high precision and accuracy and accordingly at very high cost.
2. When the spherical valve 3 is tightly fitted in the spherical recess 21, it is not easy to turn the spherical valve 3 with only one hand. And, it is, of course, very inconvenient to operate the nasal irrigator by holding the container 1 with one hand and pulling or pushing the tube 31 and the plug 4 with another in order to turn the spherical valve 3 relative to the spherical recess 21.
3. Moreover, a considerable force is needed to pull or push the tube 31 and the plug 4 in order to turn the spherical valve 3 tightly fitted in the curved lower cap 2. As a result, the curved lower cap 2 and the conduit 13 tend to become worn and separate from each other easily. This would undesirably shorten the usable life of the nasal irrigator.
4. There is not any particular means provided to secure the plug 4 to the tube 31, and the plug 4 tends to separate from the tube 31 while the nasal irrigator is in use that would cause inconvenience in the use of the nasal irrigator.

It is therefore desirable to provide an improved nasal irrigator to overcome the disadvantages of the conventional nasal irrigator.

SUMMARY OF THE INVENTION

A primary object of the present invention is to provide a nasal irrigator that can be easily handled and is therefore convenient for use.

Another object of the present invention is to provide a nasal irrigator that has a simplified structure and can therefore be manufactured with general techniques and at reduced cost.

To achieve the above and other objects, the nasal irrigator of the present invention includes a container, a lower cap, and a plug. The container contains a predetermined amount of saline or other cleaning liquid therein for washing a patient's nostril and is provided at an upper end with an upper cap having an air vent, and at a lower end with a conduit which extends downward and then bends to incline upward to define an open free end. The lower cap is fitted at a rear side to the open free end of the conduit. A front side of the lower cap extends forward to form a tube portion having an annular rib provided around an outer periphery of a front end thereof. A stopper diametrically smaller than the tube portion is fixed in the front end of the tube portion, such that the stopper projects from the front end of the tube portion and a passage is formed between the stopper and the tube portion. The plug is adapted to extend into a patient's nostril and includes a front head portion being provided with an axially extended through hole into which the stopper of the lower cap may be extended to block the through hole, and a rear sleeve portion being dimensioned to fitly but movably put around the tube portion of the lower cap and having a pair of radially inward projected annular flanges provided around an inner peripheral wall of the sleeve portion at a predetermined position to define an annular groove between the pair of annular flanges. Whereby when the plug is turned while pushed toward the lower cap, the stopper is brought into a position in the through hole of the plug to block and seal the through hole and thereby brings the nasal irrigator into a closed state, and when the plug is turned while pulled in a direction opposite to the lower cap until the annular groove in the sleeve portion engages with the annular rib around the front end of the tube portion of the lower cap, the stopper is brought to a position a distance away from the through hole, so that saline or other cleaning liquid in the container is allowed to flow into the patient's nostril via the conduit, the passage between the stopper and the tube portion, and the through hole of the plug, bringing the nasal irrigator into an open state.

BRIEF DESCRIPTION OF THE DRAWINGS

The objects, features, and functions of the present invention may be best understood by referring to the following detailed description of the preferred embodiments and the accompanying drawings, wherein.

DETAILED DESCRIPTION OF THE PREFERRED EMBODIMENTS

Figure 4:
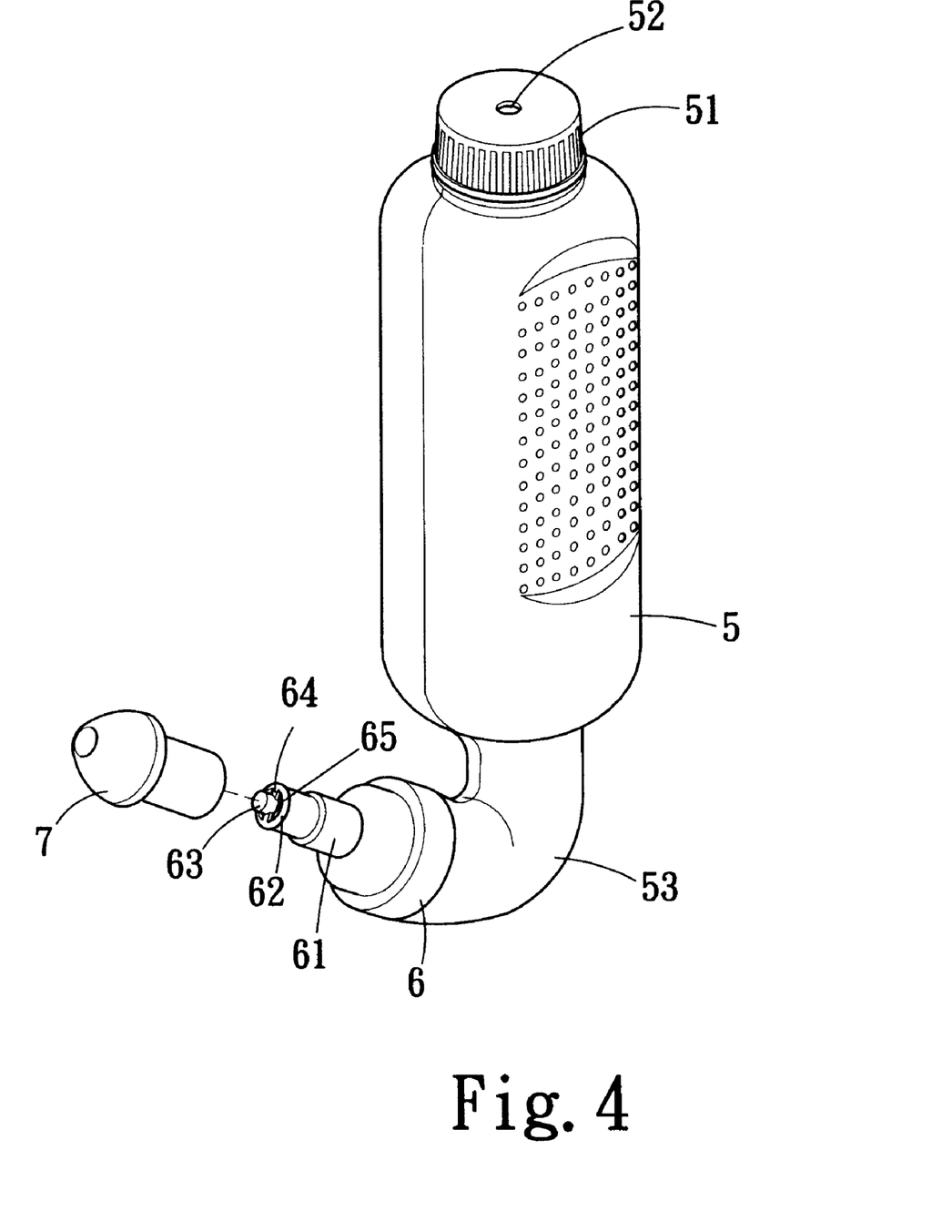
FIG. 4 is a perspective of a nasal irrigator according to the present invention with a plug thereof removed from a front end of the nasal irrigator.
Figure 5:
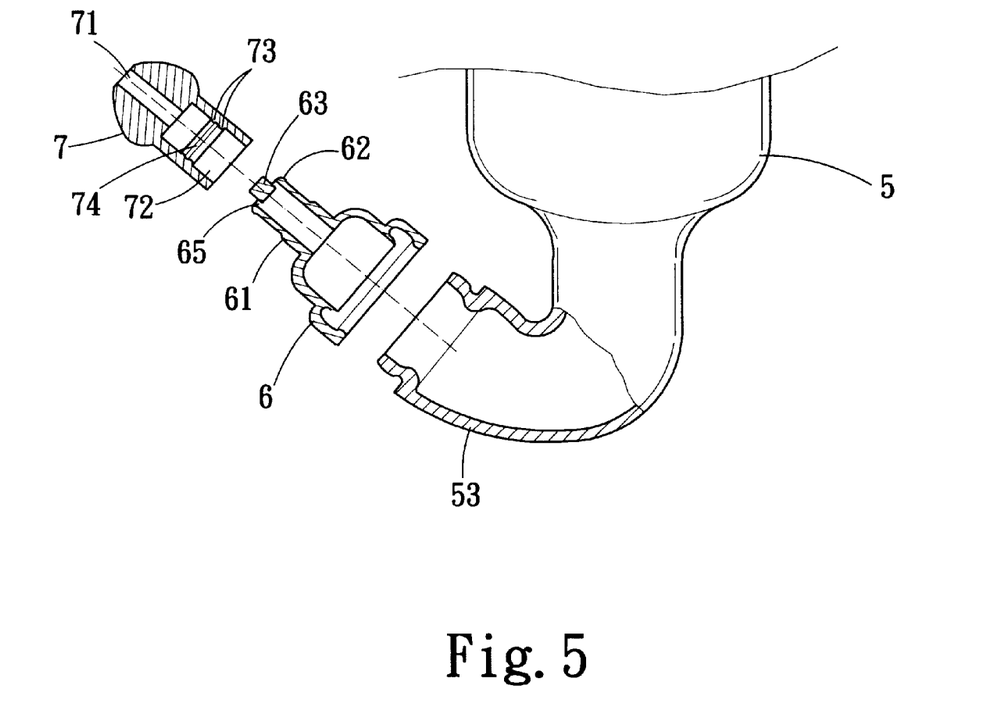
FIG. 5 is a fragmentary and exploded vertical sectional view of the nasal irrigator of FIG. 4.

Please refer to FIGS. 4 and 5 that are perspective and fragmentary and exploded vertical sectional views, respectively, of a nasal irrigator according to the present invention. As shown, the nasal irrigator mainly includes a container 5 for containing a predetermined amount of saline or other cleaning liquid therein, a lower cap 6, and a plug 7.

The container 5 is provided at an upper end with an upper cap 51 having an air vent 52, and at a lower end with a conduit 53 that extends downward by a predetermined length and then bends to incline upward at a predetermined angle, in a predetermined direction, and by a predetermined length to define an open free end thereof.

The lower cap 6 is fixedly connected at a rear open end thereof to the open free end of the conduit 53. A front end of the lower cap 6 projects forward to form a tube portion 61. The tube portion 61 is provided around an outer periphery of a front end thereof with an annular rib 62. A stopper 63 that is diametrically smaller than the tube portion 61 is connected to the front end of the tube portion 61 through two connecting bars 64 radially extended from two preferably diametrically opposite sides near a rear end of the stopper 63 to two points on an inner peripheral wall of the front end of the tube portion 61, such that the stopper 63 is radially centered in the front end of the tube portion 61 with a large portion of the stopper 63 projecting forward from the front end of the tube portion 61. A space left between an outer peripheral wall of the stopper 63 and the inner peripheral wall of the front end of the tube portion 61 forms a passage 65 that communicates an interior of the tube portion 61 with a space outside the tube portion 61.

The plug 7 includes a front head portion having a central through hole 71 axially extended through the head portion, and a rear sleeve portion 72. The through hole 71 of the head portion of the plug 7 is so sized that the stopper 63 may be extended into the through hole 71 and seals the same in a watertight manner. The sleeve portion 72 of the plug 7 is provided at an inner peripheral wall around a middle section thereof with a pair of radially inward projected annular flanges 73. An interior of the sleeve portion 72 is so sized and configured that the tube portion 61 of the lower cap 6 may be extended to fitly locate in the sleeve portion 72 with the annular rib 62 around the front end of the tube portion 61 engaging with an annular groove 74 defined between the pair of annular flanges 73.

Figure 6:
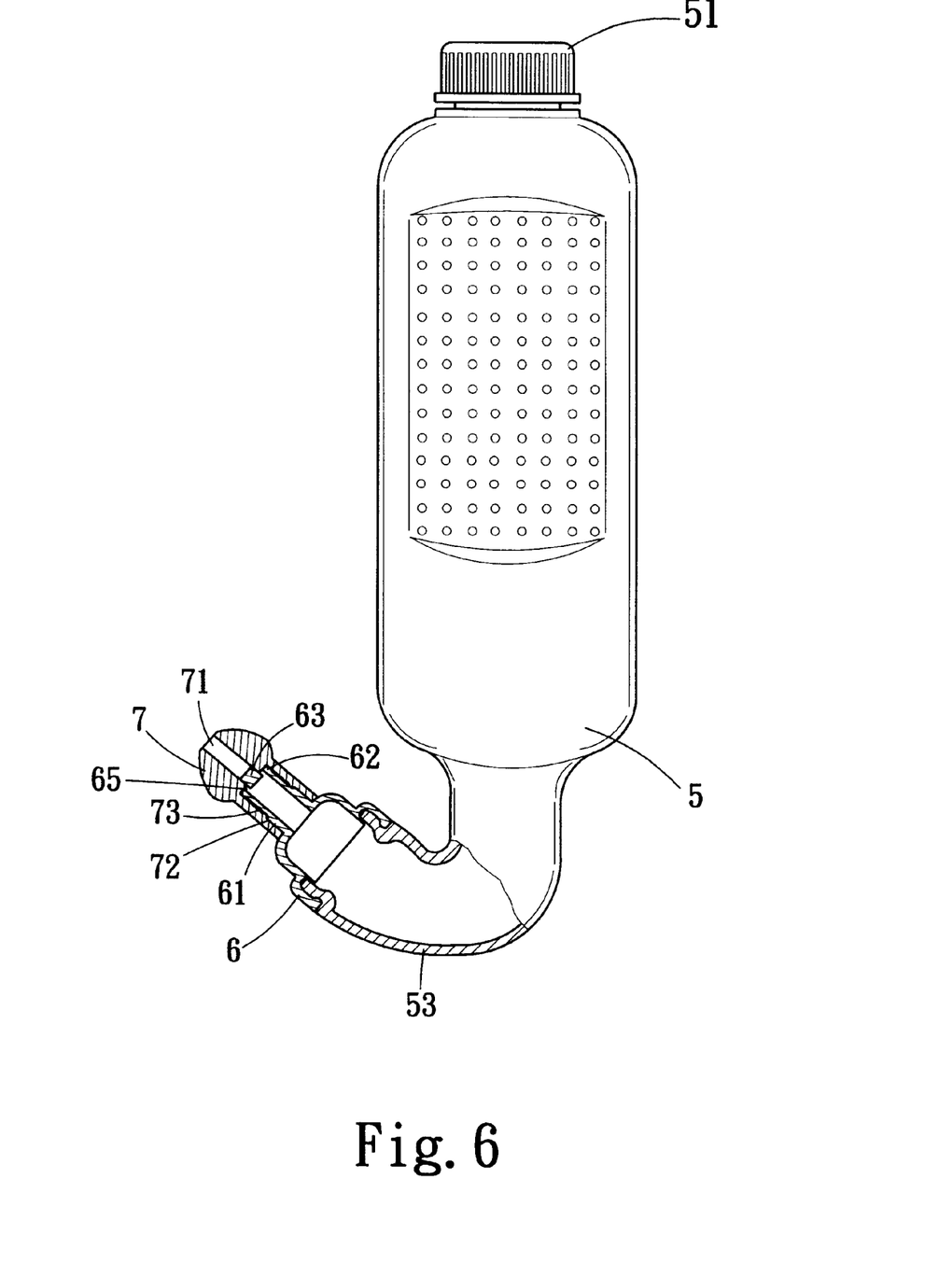
FIG. 6 is a partially vertical sectional view of the nasal irrigator of FIG. 4 in a closed state.

FIG. 6 is a partially vertical sectional view of the nasal irrigator of the present invention in a closed state. By turning while pushing the front head portion of the plug 7 toward the lower cap 6, the stopper 63 at the front end of the tube portion 61 of the lower cap 6 is brought to a position in an inner end of the through hole 71 at an interface of the head portion and the sleeve portion of the plug 7, so as to block and seal the through hole 71 at its inner end. At this point, the nasal irrigator of the present invention is closed and saline or other cleaning liquid contained in the container 5 of the nasal irrigator can flow from the container 5 via the conduit 53 to the tube portion 61 of the lower cap 6 without flowing into the through hole 71 in the head portion of the plug 7.

Figure 7:
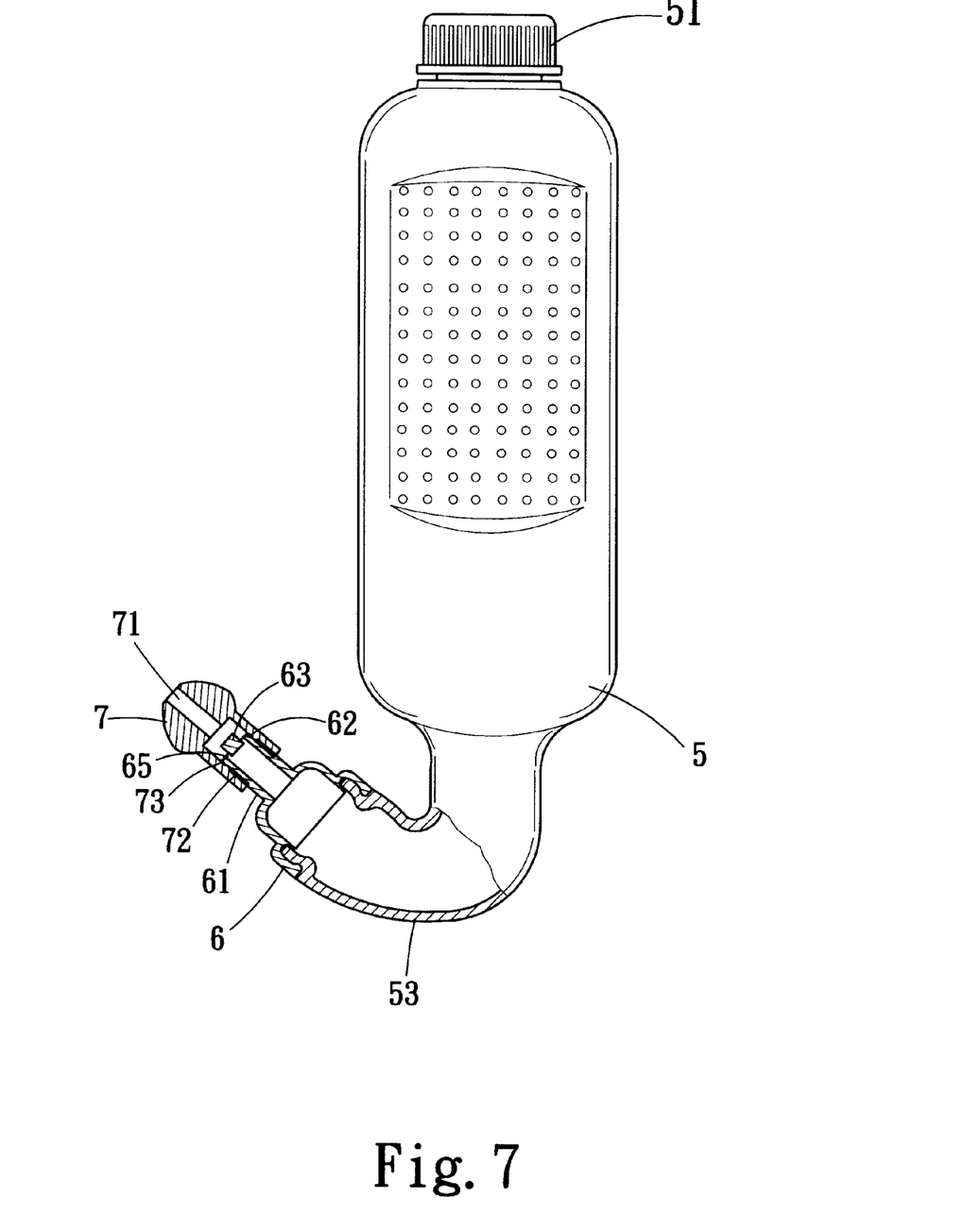
FIG. 7 is a partially vertical sectional view of the nasal irrigator of FIG. 4 in an open state.

FIG. 7 is similar to FIG. 6 but showing the nasal irrigator of the present invention in an open state. By turning while pulling the head portion of the plug 7 in a direction opposite to the lower cap 6, the stopper 63 at the front end of the tube portion 61 of the lower cap 6 is brought to a position outside the inner end of the through hole 71 in the head portion of the plug 7, so that a space exists between the stopper 63 and the through hole 71. At this point, the nasal irrigator of the present invention is opened and saline or other cleaning liquid contained in the container 5 of the nasal irrigator is allowed to flow from the container 5 and sequentially pass the conduit 53, the lower cap 6, the tube portion 61 of the lower cap 6, the passage 65 between the tube portion 61 and the stopper 63, the space existed between the stopper 63 and the inner end of the through hole 71 to enter into the through hole 71. The saline or other cleaning liquid then keeps flowing from an outer end of the through hole 71 into a patient's nostril (not shown).

To prevent the plug 7 from undesirably moving rearward toward the lower cap 6 while the plug 7 is inserted into the patient's nostril and therefore closing the through hole 71 with the stopper 63, the head portion of the plug 7 is preferably turned while pulled until the annular groove 74 defined by the pair of radially inward projected annular flanges 73 in the sleeve portion of the plug 7 engages with the annular rib 62 around the front outer periphery of the tube portion 61 of the lower cap 6.

The following are some advantages of the nasal irrigator of the present invention:

1. The nasal irrigator can be conveniently and effortless operated by turning while pulling or pushing the plug 7 with one hand and is therefore practical for use.
2. The closing of the nasal irrigator could be easily accomplished simply by blocking the through hole 71 of the plug 7 with the stopper 63 in the lower cap 6 without other complicate or precision parts, the nasal irrigator can therefore be manufactured at reduced cost.
3. The operation of the nasal irrigator of the present invention involves simple and effort-saving movements without the risk of easily damaging the parts thereof. The nasal irrigator can therefore have prolonged usable life.
4. The nasal irrigator of the present invention includes only three parts, namely, the container 5, the lower cap 6 and the plug 7. The spherical valve 3 that requires high precision is omitted to largely simplify and improve the conventional nasal irrigators.

5. The provision of the pair of annular flanges 73 enables the plug 7 to firmly associate with the tube portion 61 of the lower cap 6 without the risk of being easily separated from the tube portion 61 when the nasal irrigator is in use. The nasal irrigator is therefore more convenient for use than the conventional ones.

It is apparent that the present invention is illustrated with the description of a preferred embodiment thereof, and it is contemplated that many changes and modifications in the described embodiment can be carried out without departing from the scope of the invention which is intended to be limited only by the appended claims.

What is claimed is:

1. A nasal irrigator, comprising:

a container for containing a predetermined amount of saline or other cleaning liquid therein for cleaning a patient's nostril, and being provided at a lower end thereof with a conduit which extends downward and then bends to incline upward at an angle, to define an open free end;

a lower cap fitted at a rear side thereof to said open free end of said conduit of said container, a front side of said lower cap extending forward to form a tube portion having an annular rib provided around an outer periphery of a front end thereof, a stopper diametrically smaller than said tube portion being fixed in the front end of said tube portion, such that said stopper projects from said front end of said tube portion with a passage being formed between said stopper and said tube portion to communicate an interior of said tube portion with a space outside said tube portion; and a plug for extending into a patient's nostril, said plug including a front head portion provided with an axially extended through hole into which said stopper of said lower cap may be extended to block said through hole, and a rear sleeve portion being dimensioned to movably fit around said tube portion of said lower cap and having a pair of radially inward projected annular flanges provided around an inner peripheral wall of said sleeve portion at a predetermined position to define an annular groove between said pair of annular flanges;

whereby when said plug is turned while pushed toward said lower cap, said stopper of said lower cap is brought into a position in said through hole of said plug to block and seal said through hole, thereby bringing said nasal irrigator into a closed state; and when said plug is turned while pulled in a direction opposite to said lower cap until said annular groove in said sleeve portion engages with said annular rib around the front end of said tube portion of said lower cap, said stopper is brought to a position a distance away from said through hole, so that the saline or other cleaning liquid in said container is allowed to flow into the patient's nostril via said conduit, said passage between said stopper and said tube portion of said lower cap, and said through hole of said plug, bringing said nasal irrigator into an open state.

2. A nasal irrigator as claimed in claim 1, wherein said stopper is fixed in the front end of said tube portion through two connecting bars extending between two sides near a rear end of said stopper and two points on an inner peripheral wall of said tube portion.

3. A nasal irrigator as claimed in claim 1, wherein said container has an upper end with an upper cap having an air vent.

4. A nasal irrigator as claimed in claim 1, wherein the conduit of said container extends downward by a predetermined length, and then bends to incline upward at a predetermined angle, by a predetermined length and in a predetermined direction.

5. A nasal irrigator, comprising:

a container for containing a cleaning liquid therein, said container including a conduit through which the cleaning liquid may pass, said conduit having a bent shape;

a lower cap having a rear side attached to an open free end of said conduit of said container, and having a tube portion at a front side thereof, said lower cap further including a stopper fixed in said tube portion so as to project from said tube portion, said stopper being diametrically smaller than said tube portion so that a passage is formed between said stopper and said tube portion, the passage communicating an interior of said tube portion with a space outside said tube portion; and a plug for extending into a patient's nostril, said plug including a front head portion provided with an axially extending through hole, said plug further including a rear sleeve portion dimensioned to movable fit around said tube portion of said lower cap, said plug being movable in a linear direction toward and away from said lower cap to define respective closed and open states of said nasal irrigator;

whereby when said plug is moved in a first direction toward said lower cap, said stopper of said lower cap is brought into a position in the through hole of said plug to block and seal the through hole, thereby bringing said nasal irrigator into the closed state; and when said plug is moved in a second direction opposite to the first direction, said stopper is brought to a position a distance away from the through hole, so that the cleaning liquid in said container is allowed to flow into the patient's nostril via said conduit, the passage between said stopper and said tube portion of said lower cap, and the through hole of said plug, bringing said nasal irrigator into the open state.

6. The nasal irrigator as recited in claim 5, further comprising means for preventing an inadvertent separation between said plug and said lower cap when said nasal irrigator is in the open state.

* * * * *